US012806366B2

(12) United States Patent
Zhang et al.

(10) Patent No.: US 12,806,366 B2
(45) Date of Patent: Nov. 24, 2026

(54) HYDRODYNAMICS PARAMETER DETECTION EQUIPMENT FOR CATHETER

(71) Applicant: Shandong Branden Medical Device Co., Ltd, Shandong (CN)

(72) Inventors: Haijun Zhang, Shandong (CN); Shudi Zhi, Shandong (CN); Kunshan Yuan, Shandong (CN)

(73) Assignee: Shandong Branden Medical Device Co., Ltd., Shandong (CN)

( * ) Notice: Subject to any disclaimer, the term of this patent is extended or adjusted under 35 U.S.C. 154(b) by 625 days.

(21) Appl. No.: 18/277,777

(22) PCT Filed: Feb. 24, 2023

(86) PCT No.: PCT/CN2023/078035

§ 371 (c)(1),
(2) Date: Aug. 18, 2023

(87) PCT Pub. No.: WO2024/066185

PCT Pub. Date: Apr. 4, 2024

(65) Prior Publication Data

US 2025/0010020 A1 Jan. 9, 2025

(30) Foreign Application Priority Data

Sep. 27, 2022 (CN) ........................ 202211177575.1

(51) Int. Cl.
*A61B 5/02* (2006.01)
*A61M 25/00* (2006.01)

(52) U.S. Cl.
CPC ....... *A61M 25/00* (2013.01); *A61M 2205/103* (2013.01); *A61M 2205/3327* (2013.01);
(Continued)

(58) Field of Classification Search
None
See application file for complete search history.

(56) References Cited

U.S. PATENT DOCUMENTS

2002/0120204 A1 8/2002 Pfeiffer et al.
2006/0149393 A1* 7/2006 Calderon ........... A61M 25/1011 604/4.01

(Continued)

FOREIGN PATENT DOCUMENTS

CN 104950130 9/2015
CN 109310338 2/2019

(Continued)

OTHER PUBLICATIONS

"International Search Report (Form PCT/ISA/210) of PCT/CN2023/078035", mailed on Apr. 21, 2023, pp. 1-5.

*Primary Examiner* — Tse Chen
*Assistant Examiner* — Martin Nathan Ortega
(74) *Attorney, Agent, or Firm* — JCIPRNET

(57) ABSTRACT

A hydrodynamics parameter detection equipment for a catheter relating to the technical field of medical catheter detection equipment is provided. A pressure in a catheter is adjusted by controlling a height of a liquid level. A flow velocity is obtained by monitoring changes of a mass of liquid. Data obtained in use is processed using the least square method, thus obtaining a pressure-flow velocity relationship function to evaluate the catheter on the basis of an individual standard and a same-class standard. The present disclosure provides the detection equipment for hydrodynamics indexes of a medical catheter, and provides a data support for scoring the performance of the catheter and a catheter path. The equipment of the present disclosure is in no contact with infusion liquid, so that no pollution is caused, and the equipment can be used clinically.

10 Claims, 5 Drawing Sheets

(52) U.S. Cl.
CPC ............... *A61M 2205/3331* (2013.01); *A61M 2205/3368* (2013.01); *A61M 2205/3379* (2013.01); *A61M 2205/36* (2013.01); *A61M 2205/50* (2013.01); *A61M 2209/02* (2013.01)

(56) References Cited

U.S. PATENT DOCUMENTS

| | | | | |
|---|---|---|---|---|
| 2008/0306403 | A1 | 12/2008 | Malm | |
| 2016/0158442 | A1* | 6/2016 | Voigt .................. | A61M 5/1723 702/50 |
| 2016/0213896 | A1* | 7/2016 | Bacallao ......... | A61M 25/10184 |
| 2018/0000421 | A1 | 1/2018 | Kim | |
| 2020/0093991 | A1* | 3/2020 | Schwartz .......... | A61M 5/16827 |
| 2020/0121860 | A1* | 4/2020 | Uber, III ........... | A61M 5/16827 |
| 2020/0289750 | A1* | 9/2020 | Wolff ................ | A61M 5/16854 |
| 2021/0361170 | A1* | 11/2021 | Schwartz ........... | A61B 5/02007 |
| 2022/0233437 | A1* | 7/2022 | Borody ................ | A61K 9/0031 |

FOREIGN PATENT DOCUMENTS

| | | |
|---|---|---|
| CN | 109990993 | 7/2019 |
| CN | 115252963 | 11/2022 |

* cited by examiner

HYDRODYNAMICS PARAMETER DETECTION EQUIPMENT FOR CATHETER

CROSS-REFERENCE TO RELATED APPLICATION

This application is a 371 of international application of PCT application serial no. PCT/CN2023/078035, filed on Feb. 24, 2023, which claims the priority benefit of China application no. 202211177575.1, filed on Sep. 27, 2022. The entirety of each of the above mentioned patent applications is hereby incorporated by reference herein and made a part of this specification.

TECHNICAL FIELD

The present disclosure relates to the technical field of medical catheter detection equipment, mainly to hydrodynamics parameter detection equipment for a catheter.

BACKGROUND

Central venous catheters, peripherally inserted central catheters, and midline catheters belong to intravascular catheters, which can be placed in a large vein for a period of time to provide infusion paths for patients. However, long-time catheterization poses some common long-term complications for the catheters, such as thrombosis, venous stenosis, and insufficient flowrate. At present, these complications are usually found by medical staff only when symptoms have significantly affected the normal use of the catheters. In this case, if treatment is ineffective, it is highly likely to perform extubation, which increases the pain and treatment costs of the patients. In severe cases, it may affect later treatment of the patients (patients with poor venous conditions), causing the patients to permanently lose the infusion paths. The insufficient flow rate, the rise of a venous pressure, and the like can be found in advance by detecting hydrodynamic parameters of the catheters every time of infusion. Rotating a catheter in a small angle or adjusting a depth of the catheter eliminates "sticking to wall" caused by the fact that a tip of the catheter sticks to a vascular wall. Early thrombi are solved by thrombolysis, which prolongs the service life of the catheter and reduces the burden on the patient. At the same time, the hydrodynamics parameters of the catheters are widely collected in clinical practice, which can comprehensively evaluate different catheters and provide reference for selection of the catheters in the future. However, there is a shortage of testing methods and equipment for direct detection of hydrodynamics parameters of catheters in clinical practice, so a technical scheme is urgently needed to fill the blank.

Patent CN 104950130A discloses a flow velocity tester for a medical catheter. A flow velocity of a catheter is obtained by weighing a mass of liquid flowing out of a tail end of the catheter at a certain height, to evaluate a flow velocity performance index of the catheter in a laboratory. However, on the one hand, the liquid will be in direct contact with a water tank, a heating device, and a conveying pipeline in a detection process, and the mass of the liquid flowing out of the tail end of the catheter needs to be collected, so this equipment cannot be used for clinical detection of hydrodynamics parameters of a vascular access of a patient with a catheter. On the other hand, the equipment only has a simple calculation function and cannot record and process detected data. Therefore, it cannot achieve measurement and evaluation throughout the entire time of catheter retention.

SUMMARY

For the shortcomings in the prior art, the present disclosure provides hydrodynamics parameter detection equipment for a catheter, which is simple in structure and convenient to operate. The detection equipment can be used clinically to detect hydrodynamics parameters of a catheter located in a blood vessel and perform data processing and analysis, so as to evaluate a state of the catheter using an individual standard and a same-class standard of catheters and provide reference for medical staff.

The hydrodynamics parameter detection equipment for the catheter has the following functions:

(1) detecting a terminal venous pressure of an internal catheter;

(2) testing clinical hydrodynamics parameters of the catheter; and (3) acquiring clinical data, and evaluating a state of the catheter to provide a data basis for later construction of a range of references of internal kinetic parameters of a vascular access.

In order to achieve the above functions, the technical solution of the present disclosure is as follows:

Hydrodynamics parameter detection equipment for a catheter includes a power system, a lifting system, a measurement system, a control and processing system, a constant-temperature storage system, and an adjustment chair.

Further, the power system includes a workbench, a motor, and an actuating device, wherein the workbench is located at a bottom of the hydrodynamics parameter detection equipment for the catheter, and the motor and the actuating device are fixed inside the workbench.

Further, the lifting system includes a stand, a guide rod, a rolling screw rod, a movable cross arm, and a displacement encoder, wherein the stand is mounted above the workbench; the guide rod and the rolling screw rod are located in the stand; the movable cross arm and the stand are connected through the guide rod; and the displacement encoder is mounted at a top end of the stand.

Further, the measurement system includes a mass sensor and a fixing device; the mass sensor is in hinged connection with the movable cross arm; the fixing device is connected below the mass sensor, and the fixing device and the mass sensor are hung below the movable cross arm in a serial connection manner; and the mass sensor includes four strain gauges and a direct current voltage source.

Further, the control and processing system includes a computer, a digital collector, a digital controller, and signal wires; the computer is connected to the digital collector and the digital controller by the signal wires; and the digital collector includes a multimeter and a digital filter. The computer reduces the drift of the mass sensor through a principal component analysis (PCA) algorithm; the computer obtains data in a use process in real time, and evaluates a state of the catheter using an individual standard and a same-class standard; the data obtained by the computer in real time in the infusion process includes: a model number of the catheter, catheter usage time, a liquid type, an infusion pressure, a flow velocity at the infusion pressure, and complications; the individual standard is that first test results of the infusion liquid of the catheter are a series of arrays, and each array includes the liquid type, the infusion pressure, the flow velocity at the infusion pressure, and the complications; a pressure-flow velocity relationship curve and a functional relation $F_s=f(v)$ for different liquid types are obtained using the least square method; the same-class standard is a series of arrays reflecting that catheters of the same model number have no complications at the same catheter usage time, and each array includes the liquid type, the infusion pressure, and the flow velocity at the infusion pressure; for the same type of liquid, each flow velocity corresponds to a group of pressures, and the group of pressures are averaged to obtain a mean pressure $F_A$ at the flow velocity; and the flow velocity and the mean pressure are processed using the least square method to obtain a same-class standard curve and a functional relation $F_A=f(v)$ at the usage time.

Further, data processing is achieved by the following four steps: in a first step, data of the same catheter obtained at the same catheter usage time and the same liquid type is taken as a group; the flow velocity $v_i$ in the group of data is substituted into the functional relation corresponding to an individual standard curve to obtain an individual standard pressure $F_s$, and is substituted into the functional relation corresponding to the same-class standard curve to obtain a same-class standard pressure $F_{AS}$; the individual standard pressure $F_s$ and the same-class standard pressure $F_{AS}$ are compared with an actually measured pressure $F_i$ in sequence to obtain an individual deviation $\alpha_s=|F_S-F_i|/F_S*100\%$ and a same-class deviation $\alpha_{AS}=|F_{AS}-F_i|/F_{AS}*100\%$; and a state of the catheter is evaluated according to the two deviations; in a second step, after recording of the group of data is completed, a current pressure-flow velocity relation curve and a functional relation $F_i=f(v_i)$ are calculated; in a third step, the least square method is performed on a series of data groups of the same catheter at the same liquid type and the same flow velocity, to obtain a group of pressure change with catheter usage time curves and functional relations $F=f(t)$, and complications are input and saved; and in a fourth step, complication-free data is recorded into a same-class standard database.

Further, the constant-temperature storage system includes a barrier and a constant-temperature heating device; the barrier is an elastic barrier or a funnel-shaped barrier; and the constant-temperature heating device is mounted in the workbench and is located right below the fixing device.

Further, the adjustment chair includes an electric lifting system, a rotating shaft, and a handle; and the handle is connected to the rotating shaft to control a bending angle of the adjustment chair. The electric lifting system is mounted on a bottom of the adjustment chair.

Further, the actuating device includes an actuating gear and an actuating sleeve; the actuating sleeve is fixed in the workbench; the actuating gear and the actuating sleeve are integrally formed; the actuating gear is located between the motor and the actuating sleeve and is in rolling connection with the motor and the actuating sleeve respectively; and the motor is a servo motor.

Further, the power system, the displacement encoder, and the movable cross arm is connected together through the rolling screw rod; and the rolling screw rod is mounted in a groove of the stand, passes through the actuating sleeve, and is in threaded connection with the actuating sleeve; and a tail end of the rolling screw rod is in threaded connection with the displacement encoder.

Further, the stand is a "U"-shaped stand or a single-arm stand. Upper limiting buckles and lower limiting buckles are mounted on the stand; position control buttons including, "▲", "▼", "||", and "▶" are mounted on a side surface of the stand, representing up, down, start, and pause in sequence. A speed reduction device is mounted on a side of the stand connected to the movable cross arm, and the speed reduction device is a speed bump or a speed reducer.

Further, the fixing device is a lifting hook or a universal clamp.

Further, the computer includes an operating system, a temperature controller, a position controller, and a data processing system; the temperature controller can control a temperature at 36.5±1 °C; an input end of the position controller is connected to the digital controller; and an output end of the position controller is connected to the motor.

Further, the digital controller is connected to the displacement encoder through the signal wire.

Further, the barrier is an elastic barrier or a funnel-shaped barrier; the elastic barrier is symmetrically mounted on two sides of the "U"-shaped stand through movable buckles; the funnel-shaped barrier is used with the single-arm stand. The funnel-shaped barrier is mounted on the storage trough in a manner of making a small-opening end downward.

Further, the constant-temperature heating device includes a storage trough, a heating device, a temperature sensor, and a heat conduction filler; a depth of the storage trough is not less than 20 cm, and a cross section is square with an edge length not less than 10 cm; the temperature sensor is connected to an input end of the temperature controller; and the heating device is connected to an output end of the temperature controller.

Further, the electric lifting system of the adjustment chair can use the electric lifting system disclosed in the prior art, or can directly use a product purchased in the market. For example, the electric lifting system is composed of a top plate, a sliding rod, a supporting rod, movable nails, force transfer belt buckles, an either-rotation motor, a force transfer belt, a conveying pulley, bottom rods, and a bottom plate, wherein the either-rotation motor is fixed on the bottom plate; the plurality of bottom rods is uniformly fixed on the bottom plate; and the sliding rod is uniformly distributed on the top plate, is slidably connected to the top plate, and corresponds to the bottom rods in a vertical direction.

Further, an upper end and a lower end of the supporting rod are rotatably connected to two sides of the sliding rod and two sides of the bottom rods through the movable nails; one end of the force transfer belt is connected to an upper ⅓ position of the supporting rod through the force transfer belt buckles, and the other end of the force transfer belt bypasses the conveying pulley and is connected to the either-rotation motor; and the force transfer belt drives the supporting rod to rotate in the same direction by clockwise or anticlockwise rotation of the either-rotation motor to adjust a height of the chair.

Further, a multi-angle rotating shaft exists in the middle of the adjustment chair, and an angle opening handle is arranged at a lower right position. The handle is pulled up to adjust an angle of a chair back.

Further, the catheter is an internal catheter or an external catheter. The internal catheter is one of a midline catheter, a peripherally inserted central catheter, a central venous catheter, and an infusion port, and the external catheter is one of a remaining needle and an infusion apparatus.

The present disclosure has the following beneficial effects:

1. The detection equipment is in no contact with liquid and will not affect normal clinical treatment.

2. The detection equipment has high automation degree because it is controlled by the computer. The PCA algorithm is used, which reduces the drift of the mass sensor and improves the detection accuracy.

3. The workbench of the detection equipment is provided with a thermostat, which can maintain a temperature of infusion liquid at 36.5±1 °C to reduce stimulation to a human body and stabilize test conditions.

4. The detection equipment provides an equipment support for detection of the hydrodynamics parameters of the catheter, and evaluates the medical catheter to provide a clinical reference basis for scoring a state of a vascular access.

BRIEF DESCRIPTION OF THE DRAWINGS

In FIG. 1, 1.1: digital controller; 1.2: computer; 2.1: lower limiting buckle; 2.2: stand; 2.3: movable cross arm; 2.4: upper limiting buckle; 2.5: displacement encoder; 3.1: mass sensor; 3.2: lifting hook; 4: constant-temperature storage system; 4.1: elastic barrier; 4.2: constant-temperature heating device; 5: power system; 5.1: workbench;

in FIG. 2, 6: adjustment chair; 6.1: rotating shaft; 6.2: handle; 6.3: electric lifting system.

in FIG. 3, 4.2.1: storage trough; 4.2.2: heating device; 4.2.3: heat conduction filler; 4.2.4: temperature sensor;

in FIG. 4, 3.3: universal clamp; 2.9: position control button; 4.3: funnel-shaped barrier;

in FIG. 5, 5.2: actuating sleeve; 5.3: actuating gear; 5.4: motor; 2.6: guide rod; 2.7: rolling screw rod; 2.8: speed reduction device;

in FIG. 6, 6.3.1: top plate; 6.3.2: sliding rod; 6.3.3: supporting rod; 6.3.4.2: conveying pulley; 6.3.4.3: force transfer belt; 6.3.4.4: either-rotation motor; 6.3.5: bottom rod; 6.3.6: bottom plate;

in FIG. 7, 6.3.3.1: movable nail; and 6.3.4.1: force transfer belt buckle.

DETAILED DESCRIPTION OF THE EMBODIMENTS

Figure 1:
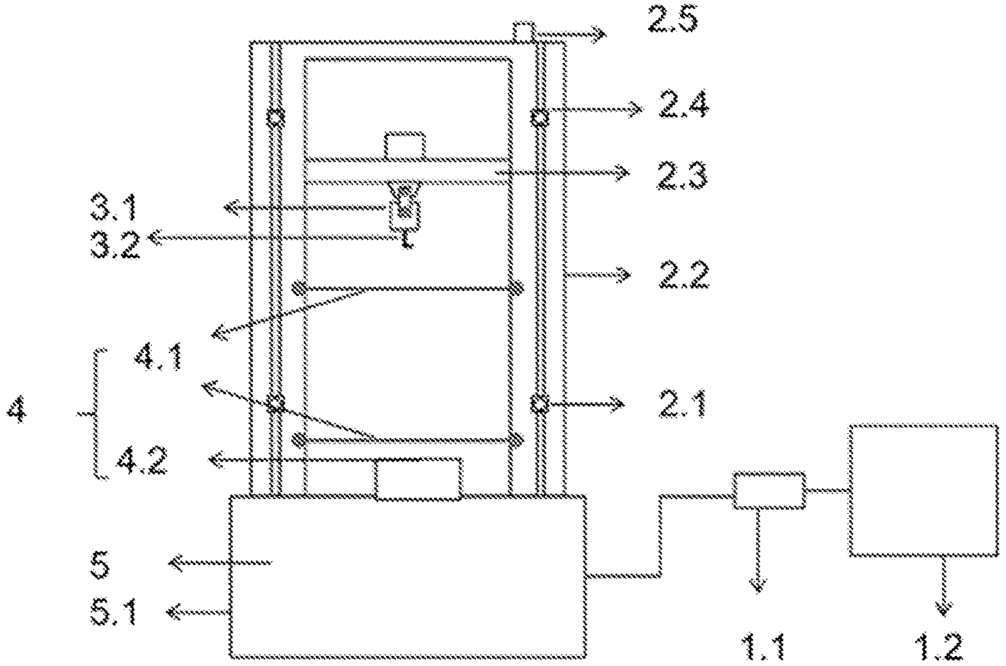
FIG. 1 is a schematic frontal structural diagram of "U"-shaped hydrodynamics parameter detection equipment for a catheter.
Figure 2:
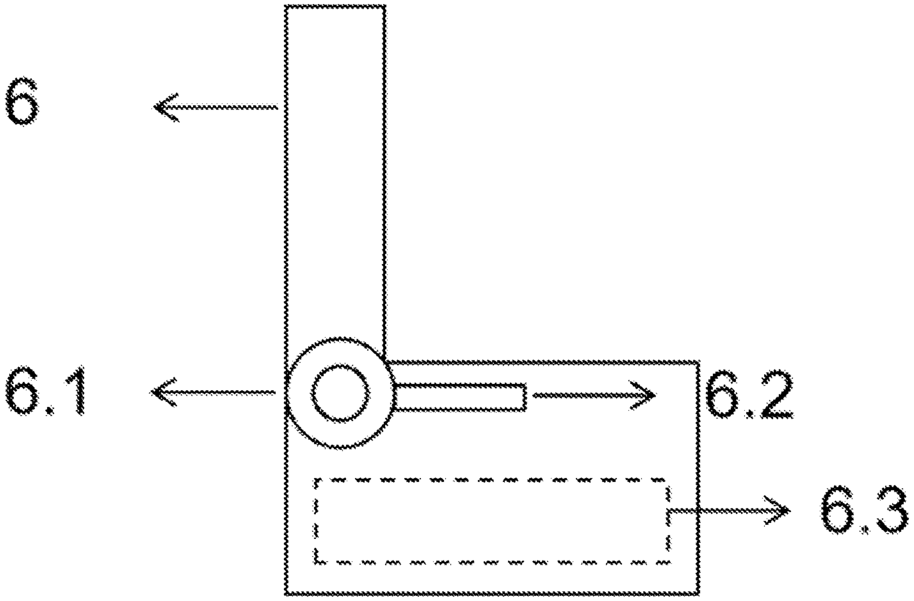
FIG. 2 is a schematic structural diagram of a liftable chair.
Figure 3:
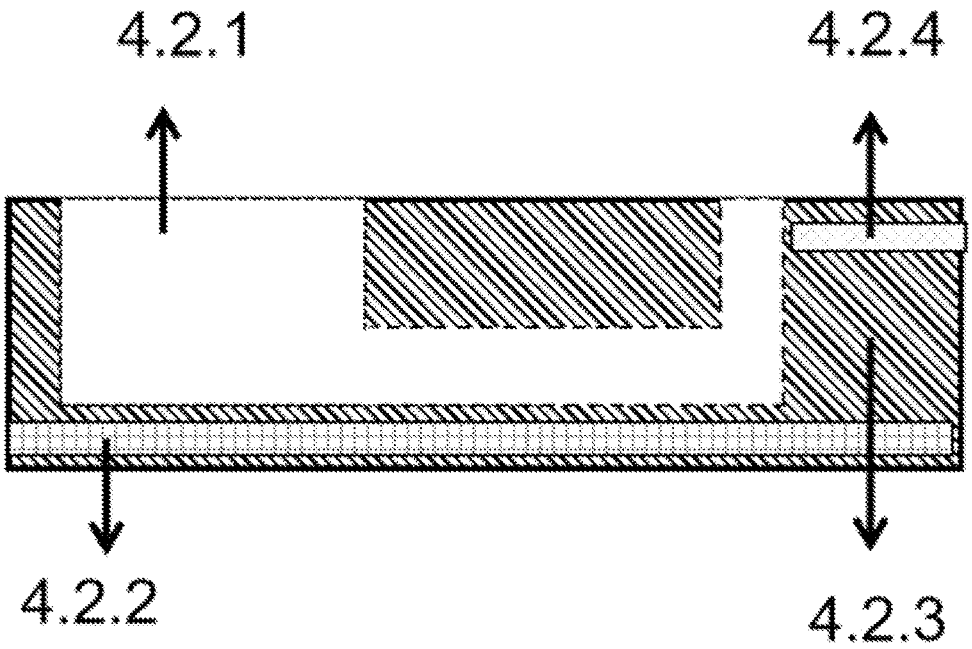
FIG. 3 is a schematic structural diagram of a side surface of a constant-temperature heating device.
Figure 4:
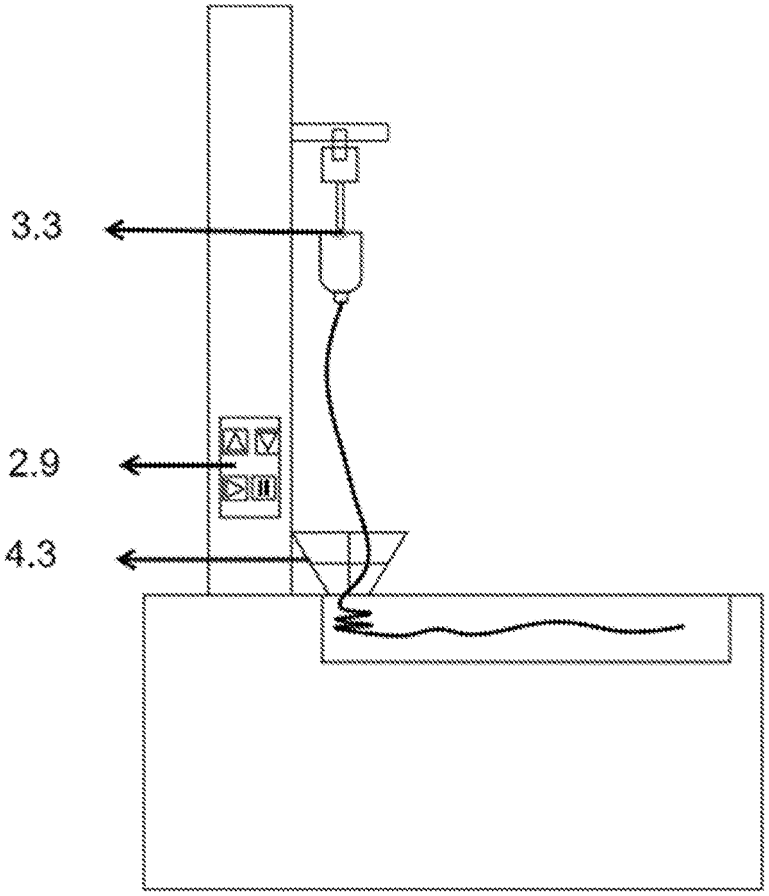
FIG. 4 is a schematic structural diagram of a side surface of a main body of single-arm hydrodynamics parameter detection equipment for a catheter.
Figure 5:
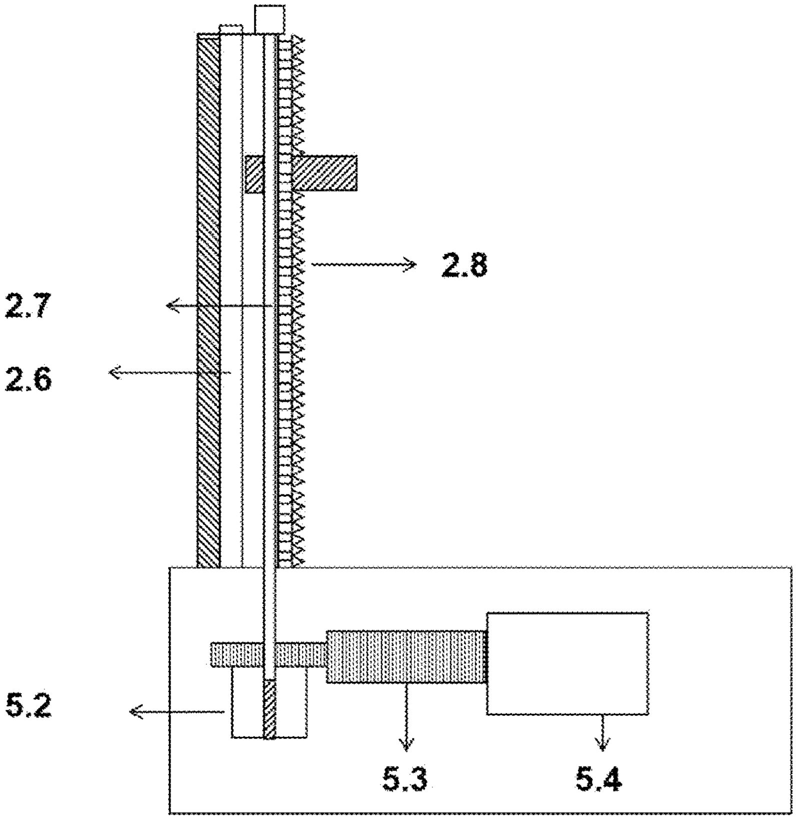
FIG. 5 is a sectional view of a side surface of workbench and a side surface of a stand of single-arm hydrodynamics parameter detection equipment for a catheter.
Figure 6:
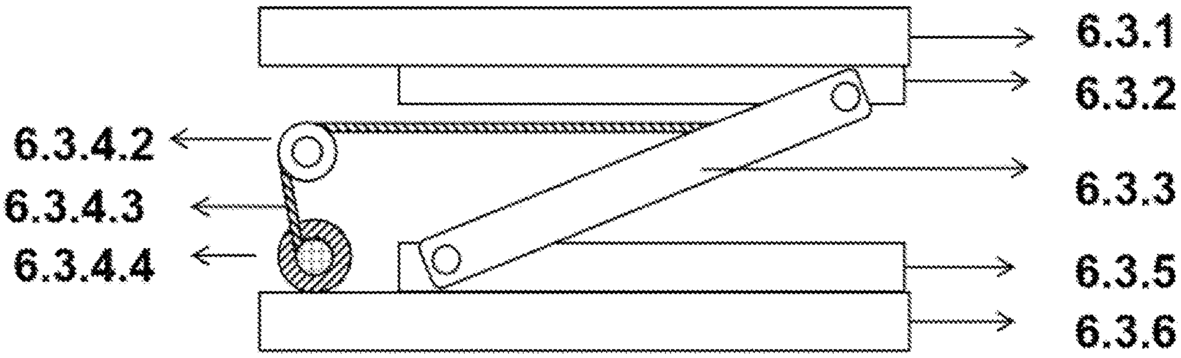
FIG. 6 is a schematic structural diagram of a front side of an electric lifting system.
Figure 7:
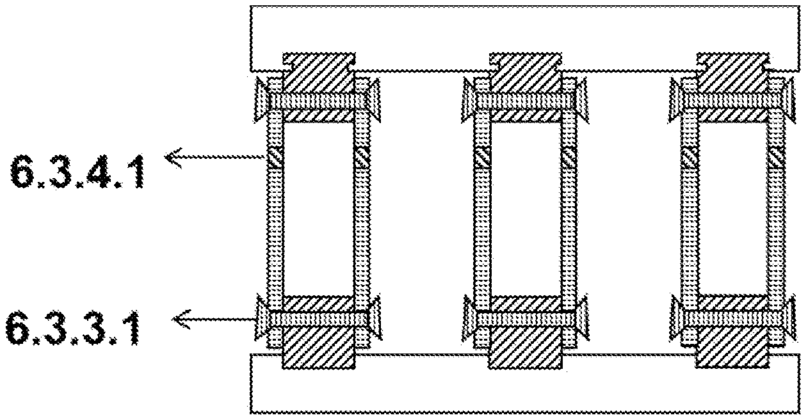
FIG. 7 is a schematic structural diagram of a side surface of an electric lifting system.
Figure 8:
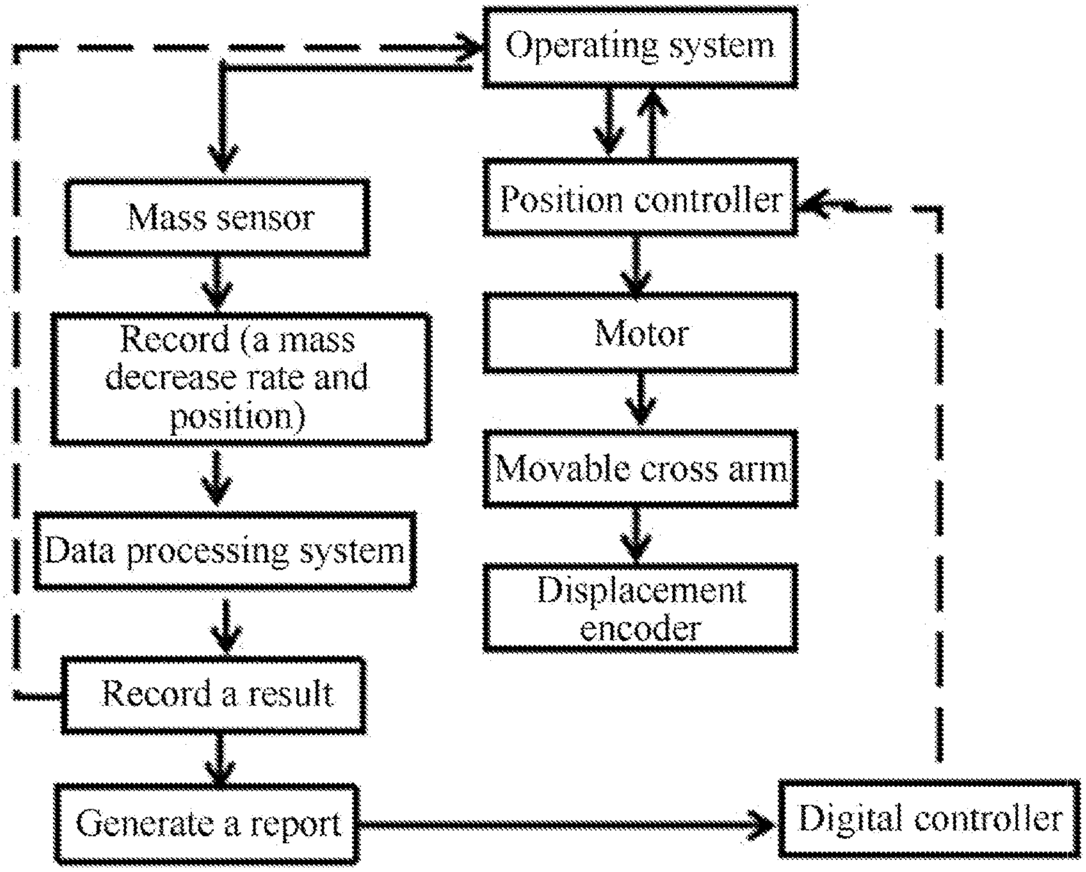
FIG. 8 is a flowchart of a control and processing system of hydrodynamics parameter detection equipment for a catheter.
Figure 9:
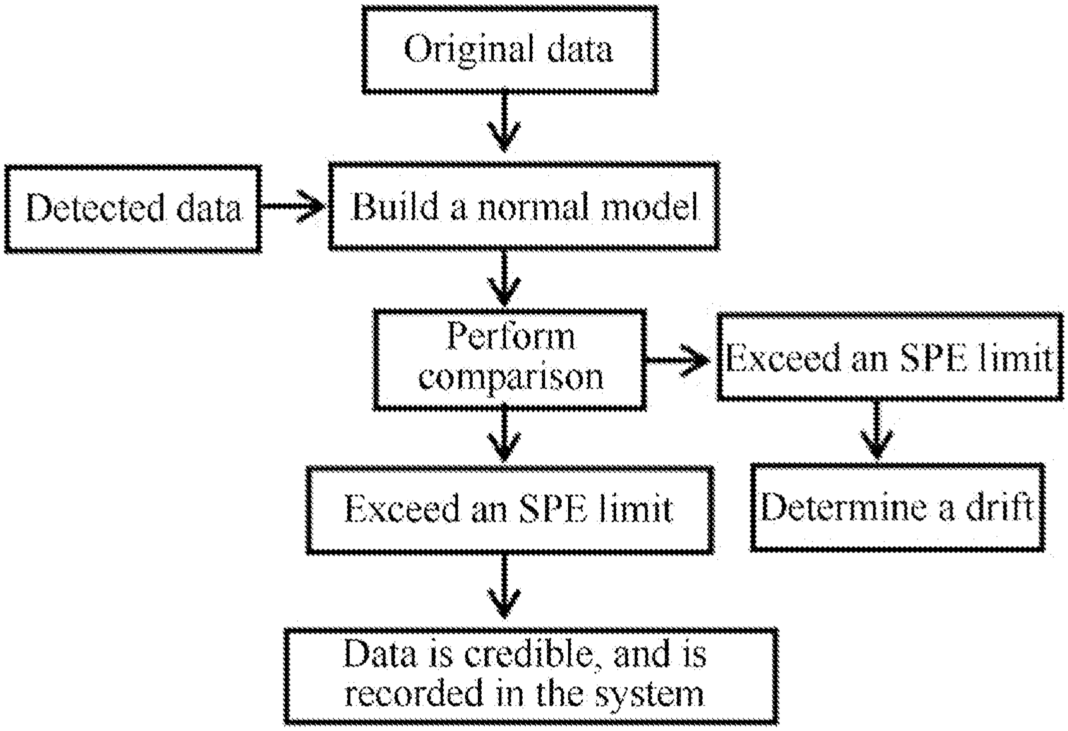
FIG. 9 is a PCA data processing process.

In order to express the objectives, technical solutions and advantages of the present disclosure more clearly, the present disclosure is described below in detail with reference to FIG. 1 to FIG. 7 and embodiments. It should be noted that a "U"-shaped stand and a single-arm stand are only different in appearance, and their functions have no difference. A lifting hook and a universal clamp are designed for different infusion bottles and infusion bags. Those with holes are fixed using the lifting hook, while those without holes are fixed using the universal clamp. Their functions have no difference. The product and an internal catheter described in the following embodiments are both intravascular catheters. Steps of device startup, software preparation, venous pressure testing, testing of an $N^{th}$ group of data, data storage and outputting, and resetting of a movable cross arm are completely consistent in different embodiments. It should be understood that the specific embodiments described here are merely to explain the present disclosure, and not intended to limit the present disclosure.

Embodiments 1 to 4 respectively describe a non-first test of a non-equipment first test catheter, a first test of the non-equipment first test catheter, a first test of an equipment first test catheter, and a non-first test of the equipment first test catheter.

Embodiment 1

Referring to FIG. 1 to FIG. 7, this embodiment relates to hydrodynamics parameter detection equipment for a catheter, including a power system, a lifting system, a measurement system, a control and processing system, a constant-temperature storage system, and an adjustment chair.

The power system includes a workbench, a motor, and an actuating device, wherein the workbench is located at a bottom of the hydrodynamics parameter detection equipment for the catheter, and the motor and the actuating device are fixed inside the workbench. The lifting system includes a stand, a guide rod, a rolling screw rod, a movable cross arm, and a displacement encoder, wherein the stand is mounted above the workbench; the guide rod and the rolling screw rod are located inside the stand; the movable cross arm and the stand are connected through the guide rod; and the displacement encoder is mounted at a top end of the stand. The measurement system includes a mass sensor and a fixing device; the mass sensor is in hinged connection with the movable cross arm; the fixing device is connected below the mass sensor, and the fixing device and the mass sensor are hung below the movable cross arm in a serial connection manner; and the mass sensor includes four strain gauges and a direct current voltage source.

Further, the control and processing system includes a computer, a digital collector, a digital controller, and signal wires; the computer is connected to the digital collector and the digital controller by the signal wires; and the digital collector includes a multimeter and a digital filter. The computer reduces a drift of the mass sensor drift through a principal component analysis (PCA) algorithm; the computer obtains data in a use process in real time, and evaluates a state of the catheter using an individual standard and a same-class standard; the data obtained by the computer in real time in the infusion process includes: a model number of the catheter, catheter usage time, a liquid type, an infusion pressure, a flow velocity at the infusion pressure, and complications; the individual standard is that first test results of the infusion liquid of the catheter are a series of arrays, and each array includes the liquid type, the infusion pressure, the flow velocity at the infusion pressure, and the complications; a pressure-flow velocity relationship curve and a functional relation $F_s=f(v)$ for different liquid types are obtained using the least square method; the same-class standard is a series of arrays reflecting that catheters of the same model number have no complications at the same catheter usage time, and each array includes the liquid type, the infusion pressure, and the flow velocity at the infusion pressure; for the same type of liquid, each flow velocity corresponds to a group of pressures, and the group of pressures are averaged to obtain a mean pressure $F_A$ at the flow velocity; and the flow velocity and the mean pressure are processed using the least square method to obtain a same-class standard curve and a functional relation $F_A=f(v)$ at the usage time.

Further, data processing is achieved by the following four steps: in a first step, data of the same catheter obtained at the same catheter usage time and the same liquid type is taken as a group; the flow velocity vi in the group of data is substituted into the functional relation corresponding to an individual standard curve to obtain an individual standard pressure $F_s$, and is substituted into the functional relation corresponding to the same-class standard curve to obtain a same-class standard pressure $F_{AS}$; the individual standard pressure $F_s$ and the same-class standard pressure $F_{AS}$ are compared with an actually measured pressure $F_i$ in sequence to obtain an individual deviation $\alpha_s=|F_S-F_i|/F_S*100\%$ and a same-class deviation $\alpha_{AS}=|F_{AS}-F_i|/F_{AS}*100\%$; and a state of the catheter is evaluated according to the two deviations; in a second step, after recording of the group of data is completed, a current pressure-flow velocity relation curve and a functional relation $F_i=f(v_i)$ are calculated; in a third step, the least square method is performed on a series of data groups of the same catheter at the same liquid type and the same flow velocity, to obtain a group of pressure change with catheter usage time curves and functional relations F=f(t), and complications are input and saved; and in a fourth step, complication-free data is recorded into a same-class standard database.

Further, the constant-temperature storage system includes a barrier and a constant-temperature heating device; the barrier is an elastic barrier or a funnel-shaped barrier; and the constant-temperature heating device is mounted in the workbench and is located right below the fixing device.

Further, the adjustment chair includes an electric lifting system, a rotating shaft, and a handle; and the handle is connected to the rotating shaft to control a bending angle of the adjustment chair. The electric lifting system is mounted on the bottom of the adjustment chair.

Further, the actuating device includes an actuating gear and an actuating sleeve; the actuating sleeve is fixed in the workbench; the actuating gear and the actuating sleeve are integrally formed; the actuating gear is located between the motor and the actuating sleeve and is in rolling connection with the motor and the actuating sleeve respectively; and the motor is a servo motor.

Further, the power system, the displacement encoder, and the movable cross arm is connected together through the rolling screw rod; and the rolling screw rod is mounted in a groove of the stand, passes through the actuating sleeve, and is in threaded connection with the actuating sleeve; and a tail end of the rolling screw rod is in threaded connection with the displacement encoder.

Further, the stand is a "U"-shaped stand or a single-arm stand. Upper limiting buckles and lower limiting buckles are mounted on the stand; position control buttons including "▲", "▼", "||", and "► " are mounted on a side surface of the stand, representing up, down, start, and pause in sequence. A speed reduction device is mounted on a side of the stand connected to the movable cross arm, and the speed reduction device is a speed bump or a speed reducer.

Further, the fixing device is a lifting hook or a universal clamp.

Further, the computer includes an operating system, a temperature controller, a position controller, and a data processing system; the temperature controller can control a temperature at 36.5±1 °C; an input end of the position controller is connected to the digital controller; and an output end of the position controller is connected to the motor.

Further, the digital controller is connected to the displacement encoder through the signal wire.

Further, the barrier is an elastic barrier or a funnel-shaped barrier; the elastic barrier is symmetrically mounted on two sides of the "U"-shaped stand through movable buckles; the funnel-shaped barrier is used with the single-arm stand. The funnel-shaped barrier is mounted on the storage trough in a manner of making a small-opening end downward.

Further, the constant-temperature heating device includes a storage trough, a heating device, a temperature sensor, and a heat conduction filler; a depth of the storage trough is not less than 20 cm, and a cross section is square with an edge length not less than 10 cm; the temperature sensor is connected to an input end of the temperature controller; and the heating device is connected to an output end of the temperature controller.

Further, the electric lifting system of the adjustment chair is composed of a top plate, a sliding rod, a supporting rod, movable nails, force transfer belt buckles, an either-rotation motor, a force transfer belt, a conveying pulley, a plurality of bottom rods, and a bottom plate, wherein the either-rotation motor is fixed on the bottom plate; the plurality of bottom rods is uniformly fixed on the bottom plate; and the sliding rod is uniformly distributed on the top plate, is slidably connected to the top plate, and corresponds to the bottom rods in a vertical direction. An upper end and a lower end of the supporting rod are rotatably connected to two sides of the sliding rod and two sides of the bottom rods through the movable nails; one end of the force transfer belt is connected to an upper ⅓ position of the supporting rod through the force transfer belt buckles, and the other end of the force transfer belt bypasses the conveying pulley and is connected to the either-rotation motor; and the force transfer belt drives the supporting rod to rotate in the same direction by clockwise or anticlockwise rotation of the either-rotation motor to adjust a height of the chair.

Further, a multi-angle rotating shaft exists in the middle of the adjustment chair, and an angle opening handle is arranged at a lower right position. The handle is pulled up to adjust an angle of a chair back.

Further, the catheter is an internal catheter and an external catheter. The internal catheter is one of a midline catheter, a peripherally inserted central catheter, a central venous catheter, and an infusion port, and the external catheter is one of a remaining needle and an infusion apparatus.

Embodiment 2

The non-first test of the non-equipment first test catheter includes the following processes:

1. Early-stage preparations: adjusting a height and angle of the adjustment chair to make a tip of an inserted catheter have the same height as the workbench, and fixing a glass infusion bottle with the universal clamp; connecting an external medical catheter to infusion liquid, connecting the external medical catheter to an internal medical catheter after the external medical catheter passes through the barrier and the storage trough to empty air, and turning off a flow velocity adjuster in an infusion apparatus to prevent the liquid from flowing.

2. Equipment startup: turning on power supplies and signal connection switches of the computer, the motor, and the digital controller, wherein the temperature controller controls the heating device according to a feedback of the temperature sensor to maintain the temperature of the constant-temperature heating device at 36.5±1 °C.

3. Software preparation: selecting a liquid type in the operating system of the computer, automatically obtaining a density of the liquid by the system, and adjusting the movable cross arm to the lower limiting buckles manually or by the computer. At the lower limiting buckles, a liquid level of the infusion liquid is flush with the workbench, and position data is zeroed.

4. Venous pressure test: selecting the venous pressure test in the operating system of the computer, completely turning on a flow rate adjuster, and increasing the height of the movable cross arm through a position control button on the side of the stand until no blood returns; then clicking the start button, making sure that the mass of the test solution will not decrease over time, clicking the confirm button, and automatically recording a position height $H_0$ at this time by software, which is a venous pressure $F_0$.

5. Hydrodynamics parameter test: selecting the hydrodynamic parameter test in the operating system of the computer; setting a pretest position $H_1$, controlling, by the position controller, the motor to turn, and driving, by the actuating device, the rolling screw rod and the movable cross arm to move to set positions; clicking the "start" button, and transmitting, by the mass sensor, a real-time mass of the test liquid; obtaining a group of vectors $x=[x_1, x_2, x_3, x_4]$ by the data processing system according to output data of the four strain gauges; normalizing the data by the software; calculating an SPE value of a statistical magnitude on the basis of a built PCA model, comparing the SPE value with a control limit calculated earlier, obtaining valid data via screening, and performing mean processing; testing, by the software a decrease of the mass of the test liquid within unit time, and converting the density of the test liquid into a volume of the liquid, calculating a flow velocity of the liquid represented by mL/min; after a value fluctuation range is ±0.01 mL/min, and outputting the position height $H_1$; calculating an injection pressure $F_1=H_1-H_0$ and testing a flow velocity $V_1$ of the liquid; clicking the "Confirm" button on a software page of the computer; recording, by the computer, the infusion pressure $F_1$ and the corresponding flow velocity $V_1$; automatically substituting, by the computer, the flow velocity $V_1$ into a relation $F_s=f(v)$ corresponding to an individual standard curve and a relation $F_A=f(v)$ corresponding to a same-class standard curve to obtain standard pressures $F_{S1}$ and $F_{AS1}$; and comparing the standard pressures with the actually measured pressure $F_1$ in sequence to obtain deviations $\alpha_{s1}=|F_{S1}-F_1/F_{S1}*100\%$ and $\alpha_{As1}=|F_{AS1}-F_1/F_{AS1}*100\%$, wherein $\alpha\leq5$ means the catheter has a good condition; in a case of $5<\alpha\leq10$, it is prompted that there is a risk; in a case of $10<\alpha\leq20$, it is prompted that processing is required; in case of $\alpha>20$, the system sounds an alarm; if "Retest" is clicked, results are not saved, and the test is restarted.

6. Test of an $N^{th}$ group of data: setting a position $H_N$, and controlling, by the position controller, the motor to drive the rolling screw rod through the actuating device, thus moving the movable cross arm to the set position; and clicking the start button, and repeating the process for 5 times to obtain a pressure $F_N=H_N-H_0$, a flow velocity $V_N$, and a deviation.

7. Data storage and outputting: after the test is completed, selecting current test data, and clicking "Generate image" so that the computer uses the least square method to obtain a current test curve and a pressure-flow velocity functional relation; selecting data acquired at different usage time of the product, screening a specific liquid type and a pressure value at a flow velocity to obtain a group of pressures; clicking "Generate image" so that the computer uses the least square method to obtain a pressure change with usage time curve and a functional relation F=f(t); clicking "Generate report" to generate an experimental report, and displaying a test result.

8. Resetting of the movable cross arm: after the infusion of the liquid is completed, turning off the flow rate adjuster, setting a position at "0", moving the movable cross arm to the lower limiting buckles, replacing the infusion liquid or cutting off connection between the external medical catheter and the internal medical catheter, and performing conventional sealing on the internal medical catheter to prevent blood return.

9. Database updating: determining and selecting, by medical staff, whether complications are found during current use, then selecting to import this group of data into a database, selecting "Product model number", "Product usage time", "Liquid type", and "No complications", clicking "Data screening" to obtain pressure-flow velocity data of all products with this model number that can normally infuse the same type of liquid at the same usage time, averaging pressures at the same flow velocity to obtain:

$$F_A = \frac{\sum_{j=1}^{n} F_j}{n},$$

obtaining a mean pressure-flow velocity curve and a relation $F_A=f(v)$ by using the least square method, clicking "Save" and updating the same-class standard curve and the functional relation.

Embodiment 3

An implementation of the first test of the non-equipment first test catheter is basically the same as Embodiment 1, but a difference is as follows: As a certain product is used for the first time, the calculated deviations are only compared with the same-class standard in the test of the hydrodynamics parameters. Specifically, the computer records an infusion pressure $F_1$ and a corresponding flow velocity $V_1$; and the computer automatically substitutes a flow velocity V into the relation $F_A=f(v)$ corresponding to the same-class standard curve to obtain a standard pressure $F_{AS1}$, and compares the standard pressure with the actually measured pressure $F_1$ to obtain a deviation $\alpha_{AS1}=|F_{AS1}-F_1|/F_{AS1}*100\%$, wherein $\alpha_{As1}\leq5$ means the catheter has a good condition; in a case of $5<\alpha_{As1}\leq10$, it is prompted that there is a risk; in a case of $10<\alpha_{As1}\leq20$, it is prompted that processing is required; and in case of $\alpha_{As1}>20$, the system sounds an alarm.

Embodiment 4

The first test of the equipment first test catheter is basically the same as Embodiment 2, but a difference is as follows:

1. One step is added in the early-stage preparation: building a normal model of the mass sensor after mounting: acquiring data output in normal cases within a range limit of the sensor by using standard weights (1 Kg, 500 g, 250 g, and 1 g):

$$X = \begin{bmatrix} x_{11} & x_{12} & x_{13} & x_{14} \\ x_{21} & x_{22} & x_{23} & x_{24} \\ x_{31} & x_{32} & x_{33} & x_{34} \\ x_{41} & x_{42} & x_{43} & x_{44} \end{bmatrix}$$

normalizing X to eliminate false variation effects caused by different dimensions:

$$X_S = \frac{[x-(1\ 1\ 1\ 1)^T M]}{\sqrt{\mathrm{diag}(\sigma_1^2\ \sigma_2^2\ \sigma_3^2\ \sigma_4^2)}}$$

where $M=[m_1, m_2, m_3, m_4]$ is a mean value of a variable x; diag is a logarithmic matrix; $\sigma^2$ is a variance;

performing singular decomposition on $X_S$:

$$X_S = t_1 v_1^T + t_2 v_2^T + t_3 v_3^T + t_4 v_4^T$$

where $t_i$ is a component vector of an $i^{th}$ principal element, and vi is an $i^{th}$ load vector;

calculating four feature values of $X_S$, and sorting the feature values from large to small, namely: $\lambda_1$, $\lambda_2$, $\lambda_3$, and $\lambda_4$:

determining a quantity of principal elements by accumulating principal element contribution rates and using a percentage method, wherein a variance contribution rate $\sigma_i$ of the $i^{th}$ principal element is:

$$\sigma_i = \frac{\lambda_i}{\sum_{i=1}^{4} \lambda_i}$$

where $\lambda_i$ is a feature value of $X_S$, which replaces the variance of the $i^{th}$ principal element during calculation an accumulated variance contribution rate S of the previous h principal elements is:

$$S = \frac{\sum_{i=1}^{h} \lambda_i}{\sum_{i=1}^{4} \lambda_i}$$

when S is greater than 85%, the quantity of the principal elements is h, and a control limit of a squared prediction error (SPE) is determined.

2. Test of the hydrodynamics parameters: only performing data storage. Specifically, the computer records an infusion pressure $F_1$ and a corresponding flow velocity $V_1$.

3. Database updating: determining and selecting, by medical staff, whether complications are found during current use, and then selecting to import this group of data into a database.

Embodiment 5

The non-first test of the equipment first test catheter is basically the same as Embodiment 1, but a difference is as follows: In the test of the hydrodynamics parameters, the computer automatically substitutes a flow velocity $V_1$ into the relation $F_s=f(v)$ corresponding to the individual standard curve to obtain a standard pressure $F_{S1}$, and compares the standard pressure with the actually measured pressure $F_1$ to obtain a deviation $\alpha_{s1}=|F_{S1}-F_1|/F_{S1}*100\%$, wherein $\alpha_{s1}\leq 5$ means the catheter has a good condition; in a case of $5<\alpha_{s1}\leq 10$, it is prompted that there is a risk; in a case of $10<\alpha_{s1}\leq 20$, it is prompted that processing is required; and in case of $\alpha_{s1}>20$, the system sounds an alarm. If "Retest" is clicked, results are not saved, and the test is restarted.

What is claimed is:

1. A hydrodynamics parameter detection equipment for a catheter, comprising a power system, a lifting system, a measurement system, a control and processing system, a constant-temperature storage system, and an adjustment chair, wherein the power system comprises a workbench, a motor, and an actuating device, wherein the workbench is located at a bottom of the hydrodynamics parameter detection equipment, and the motor and the actuating device are fixed inside the workbench;

the lifting system comprises a stand, a guide rod, a rolling screw rod, a movable cross arm, and a displacement encoder, wherein the stand is mounted above the workbench; the guide rod and the rolling screw rod are located inside the stand; the movable cross arm and the stand are connected through the guide rod; the displacement encoder is mounted at a top end of the stand;

the measurement system comprises a mass sensor and a fixing device; the mass sensor is in hinged connection with the movable cross arm; the fixing device is connected below the mass sensor, and the fixing device and the mass sensor are hung below the movable cross arm in a serial connection manner; the mass sensor comprises four strain gauges and a direct current voltage source;

the control and processing system comprises a computer, a digital collector, a digital controller, and signal wires; the computer is connected to the digital collector and the digital controller by the signal wires; the digital collector comprises a multimeter and a digital filter;

the computer reduces a drift of the mass sensor through a principal component analysis algorithm; the computer obtains data in an infusion process in real time, and evaluates a state of the catheter using an individual standard and a same-class standard; the data obtained by the computer in real time of the infusion process comprises: a model number of the catheter, catheter usage time, a liquid type, an infusion pressure, a flow velocity at the infusion pressure, and complications; the individual standard is first test results of an infusion liquid of the catheter which are in a series of arrays, and each array of the series of arrays comprises the liquid type, the infusion pressure, the flow velocity at the infusion pressure, and the complications; a pressure-flow velocity relationship curve which is an individual standard curve and a functional relation for different liquid types which are obtained using a least square method; the same-class standard is the series of arrays reflecting that catheters of the model number have no complications at the catheter usage time, and each array of the series of arrays comprises the liquid type, the infusion pressure, and the flow velocity at the infusion pressure; for the liquid type, the flow velocity corresponds to a group of pressures, and the group of pressures are averaged to obtain a mean pressure $F_A$ at the flow velocity; the flow velocity and the mean pressure are processed using the least square method to obtain a same-class standard curve and a functional relation at the catheter usage time;

data processing is achieved by the following four steps:

in a first step, data of the catheter obtained at the catheter usage time and the liquid type is taken as a group; the flow velocity vi in the group of data is substituted into the functional relation corresponding to the individual standard curve to obtain an individual standard pressure $F_s$, and is substituted into the functional relation corresponding to the same-class standard curve to obtain a same-class standard pressure $F_{AS}$; the individual standard pressure $F_s$ and the same-class standard pressure $F_{AS}$ are compared with an actually measured pressure $F_i$ in sequence to obtain an individual deviation $\alpha_s=|F_S-F_i|/F_S*100\%$ and a same-class deviation $\alpha_{AS}=|F_{AS}-F_i|/F_{AS}*100\%$; and a state of the catheter is evaluated according to the individual deviation and the same-class deviation;

in a second step, after recording of the group of data is completed, a current pressure-flow velocity relation curve and a functional relation are calculated;

in a third step, the least square method is performed on a series of data groups of the catheter at the liquid type and the flow velocity, to obtain a group of pressure change with catheter usage time curves and functional relations, and complications are input and saved; and in a fourth step, complication-free data is recorded into a same-class standard database;

the constant-temperature storage system comprises a barrier and a constant-temperature heating device; the barrier is an elastic barrier or a funnel-shaped barrier; the constant-temperature heating device is mounted in the workbench and is located right below the fixing device;

the adjustment chair comprises an electric lifting system, a rotating shaft, and a handle; the handle is connected to the rotating shaft to control a bending angle of the adjustment chair.

2. The hydrodynamics parameter detection equipment for the catheter according to claim 1, wherein the actuating device comprises an actuating gear and an actuating sleeve; the actuating sleeve is fixed in the workbench; and the actuating gear is located between the motor and the actuating sleeve and is in rolling connection with the motor and the actuating sleeve.

3. The hydrodynamics parameter detection equipment for the catheter according to claim 2, wherein the power system, the displacement encoder, and the movable cross arm are connected together through the rolling screw rod; and the rolling screw rod is in threaded connection with the actuating sleeve and the displacement encoder.

4. The hydrodynamics parameter detection equipment for the catheter according to claim 1, wherein the stand is a multi-segment stand having a top segment and two parallel side segments extending downward from two ends of the top segment or a single-arm stand; upper limiting buckles, lower limiting buckles, and movable buckles are mounted on the multi-segment stand; only the upper limiting buckles and the lower limiting buckles are mounted on the single-arm stand; and position control buttons comprising an up button, a down button, a start button, and a pause button are mounted on a side surface of the multi-segment stand or the single-arm stand, representing up, down, start, and pause in sequence.

5. The hydrodynamics parameter detection equipment for the catheter according to claim 4, wherein the elastic barrier is symmetrically mounted on two sides of the multi-segment stand through the movable buckles, and the funnel-shaped barrier is used with the single-arm stand.

6. The hydrodynamics parameter detection equipment for the catheter according to claim 1, wherein a speed reduction device is mounted on a side of the stand connected to the movable cross arm.

7. The hydrodynamics parameter detection equipment for the catheter according to claim 1, wherein the fixing device is a lifting hook or a universal clamp.

8. The hydrodynamics parameter detection equipment for the catheter according to claim 1, wherein the computer comprises an operating system, a temperature controller, a position controller, and a data processing system; the digital controller is connected to the displacement encoder through the signal wires; the temperature controller controls a temperature to a set range; an input end of the position controller is connected to the digital controller; and an output end of the position controller is connected to the motor.

9. The hydrodynamics parameter detection equipment for the catheter according to claim 1, wherein the constant-temperature heating device comprises a storage trough, a heating device, a temperature sensor, and a heat conduction filler; the temperature sensor is connected to an input end of a temperature controller; the heating device is connected to an output end of the temperature controller; and the funnel-shaped barrier is mounted on the storage trough in a manner of making a small-opening end downward.

10. The hydrodynamics parameter detection equipment for the catheter according to claim 1, wherein the catheter is one of a midline catheter, a peripherally inserted central catheter, a central venous catheter, an infusion port, a remaining needle, and an infusion apparatus.

* * * * *